(12) United States Patent
Cassone

(10) Patent No.: US 6,500,134 B1
(45) Date of Patent: Dec. 31, 2002

(54) METHOD FOR TREATING CIRCULATORY DISORDERS WITH ACOUSTIC WAVES

(76) Inventor: Alphonse Cassone, 2626 S. Rainbow Blvd., #109, Las Vegas, NV (US) 89146

(*) Notice: Subject to any disclaimer, the term of this patent is extended or adjusted under 35 U.S.C. 154(b) by 14 days.

(21) Appl. No.: 09/619,358

(22) Filed: Jul. 19, 2000

(51) Int. Cl.[7] .................................................. A61H 1/00
(52) U.S. Cl. ............................. 601/47; 601/46; 128/898

(56) References Cited

U.S. PATENT DOCUMENTS

| | | | | |
|---|---|---|---|---|
| 4,507,816 A | * | 4/1985 | Smith, Jr. ...................... | 5/451 |
| 5,132,942 A | * | 7/1992 | Cassone ...................... | 367/159 |
| 5,727,556 A | * | 3/1998 | Weth et al. ............. | 128/660.03 |
| 6,027,463 A | * | 2/2000 | Moriyasu ...................... | 601/46 |

* cited by examiner

Primary Examiner—Michael A. Brown
Assistant Examiner—Benjamin K. Koo
(74) Attorney, Agent, or Firm—Jeffrey Weiss; Harry M. Weiss; Weiss, Moy & Harris, P.C.

(57) ABSTRACT

A method for treating circulatory disorders by exposing the sufferer to acoustic waves from a transducer immersed in liquid. The person is preferably placed between one and twenty feet from the wave source, and is preferably exposed to waves at a frequency of about 600 Hertz for approximately twenty five minutes.

16 Claims, 1 Drawing Sheet

METHOD FOR TREATING CIRCULATORY DISORDERS WITH ACOUSTIC WAVES

FIELD OF THE INVENTION

This invention relates generally to methods for treating circulatory disorders and, more specifically, to a method for treating circulatory disorders through the use of acoustic waves.

BACKGROUND OF THE INVENTION

There are numerous disorders that effect the circulatory system of human and animal bodies. These include the following: atherosclerosis, coronary artery disease, ischemic heart disease, angina pectoris, and certain forms of impotence. The effective treatment of these disorders, and the pain, discomfort and other effects they cause, is obviously a matter for concern.

Some background information regarding these disorders, their causes, their effects on the body, and their treatments, illustrate the foregoing:

Atherosclerosis is a thickening or hardening of the arteries caused by a build-up of plaque in the inner lining of an artery. The plaque is made up of fatty substances, cholesterol, cellular waste products, calcium and fibrin. The plaque can partially or totally block the flow of blood through an artery, and can cause bleeding/hemorrhaging into the plaque or the formation of a blood clot on the surface of the plaque. When the hemorrhaging or clot blocks an entire artery, a heart attack or stroke may result.

The name coronary artery disease describes the condition where the coronary arteries have become sufficiently narrowed that the flow of blood to the heart is reduced. (One of the possible causes of such narrowing is atherosclerosis.) Ischemia is another name for reduced blood flow. A reduced flow of blood to the heart results in coronary heart disease, in which the heart muscle is damaged as a result of receiving an inadequate amount of blood due to an obstruction of its blood supply. Symptoms of coronary artery disease range from mild angina, discussed below, to a full-scale heart attack. These symptoms generally begin when there is about a 75% narrowing of a coronary artery. Approximately 13,900,000 Americans suffer from coronary heart disease, and it is the leading cause of death in the United States.

One symptom of coronary heart disease is angina pectoris, a recurring chest pain or discomfort that occurs when the heart does not receive as much blood as it needs for a particular level of work. The symptoms of angina are usually triggered by physical exertion, although they may also be triggered by emotional stress, extreme cold or heat, a heavy meal, alcohol, or smoking. The pain of angina may usually be relieved by resting or with angina medication, such as nitroglycerin, beta-blockers, and calcium channel blockers. Preferably, the underlying coronary disease causing the angina should be treated as well.

Coronary disease may be treated by the control of risk factors, such as high blood pressure, cigarette smoking, high blood cholesterol levels, and excess weight. Drug therapy is also available, including beta blockers and clot-dissolving agents. Where these are insufficient, invasive procedures such as cardiac catheterization, cardiac angiography, coronary artery bypass grafting, and angioplasty may be utilized.

Impotence, or erectile dysfunction, refers to the consistent inability to sustain an erection sufficient for sexual intercourse. It affects between 10 and 15 million American men. Impotence usually has a physical cause, and any disorder that impairs blood flow in the penis may cause impotence. One of the most common causes of impotence is damage to arteries. Diseases relating to circulation, including atherosclerosis and vascular disease, also account for a significant percentage of the cases of impotence.

Treatments for impotence, following the elimination of potential harmful drugs and behavior modifications, include vacuum devices, oral drugs (such as Viagra®), locally injected drugs, and surgically implanted devices.

It should be clear then that each of these disorders presents a problem to those who are afflicted, and that safe and effective treatments are desirable. With respect to treatment methods, non-invasive, non-surgical techniques are generally preferred to surgery. Moreover, safe non-chemical treatments are generally preferred to the use of medications, which can have foreseen or unforeseen side-effects on the body. While the individual disorders listed here have different causes, the fact that they all relate to the circulatory system raises the possibility that a single treatment could potentially work for each of these disorders. The present invention is directed to a treatment for each of these disorders—a treatment that is non-invasive, non-surgical, and non-chemical.

In U.S. Pat. No. 5,132,942, issued to applicant herein, a low frequency electroacoustic transducer (the "Cassone Transducer") is disclosed. According to U.S. Pat. No. 5,132,942, the Cassone Transducer could be used to efficiently disperse emulsions, chemical and other wastes, and the like for recycling and environmental enhancement. The Patent does not disclose the use of the Cassone Transducer for medical purposes. It is to that use that the current invention is directed.

SUMMARY OF THE INVENTION

It is an object of this invention to provide a non-invasive method for treating circulatory disorders.

It is a further object of this invention to provide a non-surgical method for treating circulatory disorders.

It is a still further object of this invention to provide a non-chemical method for treating circulatory disorders.

It is a still further object of this invention to provide a method for treating circulatory disorders through the use of acoustic waves.

BRIEF DESCRIPTION OF THE PREFERRED EMBODIMENTS

In accordance with one embodiment of the present invention, a method for treating circulatory disorders is disclosed. The method comprises the steps of: providing a low frequency sonic transducer; immersing the low frequency sonic transducer in a liquid-containing container; positioning a person having a circulatory disorder a therapeutically beneficial distance from the low frequency sonic transducer; and exposing the person for a therapeutically beneficial period of time to acoustic waves from the low frequency sonic transducer at a therapeutically beneficial frequency method for treating inflammatory musculoskeletal connective tissue disorders is disclosed.

In accordance with another embodiment of the present invention, a method for treating circulatory disorders is disclosed. The method comprises he steps of: providing a low. frequency sonic transducer; immersing the low frequency sonic transducer in a liquid-containing container; positioning a person having a circulatory disorder between approximately one foot and approximately twenty feet from the low frequency sonic transducer from the low frequency sonic transducer; and exposing the person for between approximately fifteen minutes and forty-five minutes to acoustic waves from the low frequency sonic transducer at approximately six hundred Hertz.

In accordance with still another embodiment of the present invention, a method for treating circulatory disorders is disclosed. The method comprises the steps of: Providing a low frequency sonic transducer; immersing the low frequency sonic transducer in a liquid-containing container; positioning at least a portion of a body a person having a circulatory disorder in the liquid-containing container; and exposing the person for between approximately fifteen minutes and forty-five minutes to acoustic waves from the low frequency sonic transducer at approximately six hundred Hertz.

DETAILED DESCRIPTION OF THE PREFERRED EMBODIMENTS

The present invention is concerned with an improved method for treating circulatory disorders. Such disorders include but are not limited to: atherosclerosis, coronary artery disease, ischemic heart disease, angina pectoris, and certain forms of impotence.

Figure 2:
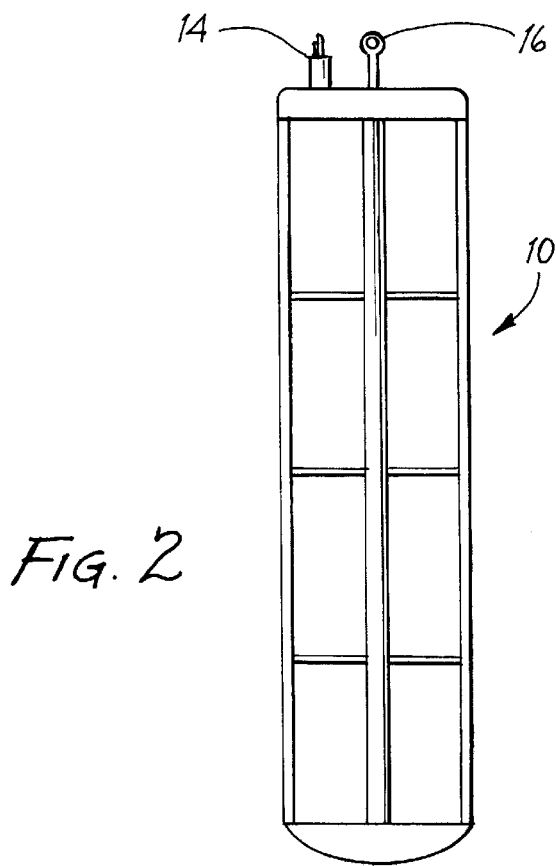
FIG. 2 is a side, cross-sectional view of an electroacoustic transducer of the type preferably used in the method of the present invention.

The method begins with the placement of a transducer 10 like the Cassone Transducer in a container 12 containing water or another liquid. The container 12 preferably has a volume ranging from one to five hundred gallons, with a volume of between five and fifty five gallons regarded as particularly preferred and a volume of approximately fifty gallons regarded as optimal. Preferably, the transducer 10 is modified slightly from the Cassone Transducer shown in U.S. Pat. No. 5,132,942 by the addition of a water-tight electrical connector 14 to replace the coaxial supply line and terminal 10 shown in FIG. 2 of U.S. Pat. No. 5,132,942, and an eye-bolt 16 to replace the pair of lift members 12 shown in FIG. 2 of U.S. Pat. No. 5,132,942. These modifications are intended to facilitate the dedicated use of the transducer 10 in a liquid environment, with the water-tight electrical connector 14 providing increased safety and the eye-bolt 16 making more easy the removal of the transducer 10 from the container 12. (While a modified Cassone Transducer as described herein is preferred for the transducer 10, any transducer capable of operating in a liquid environment and of generating acoustic waves at frequencies within the ranges described below would suffice.)

Figure 1:
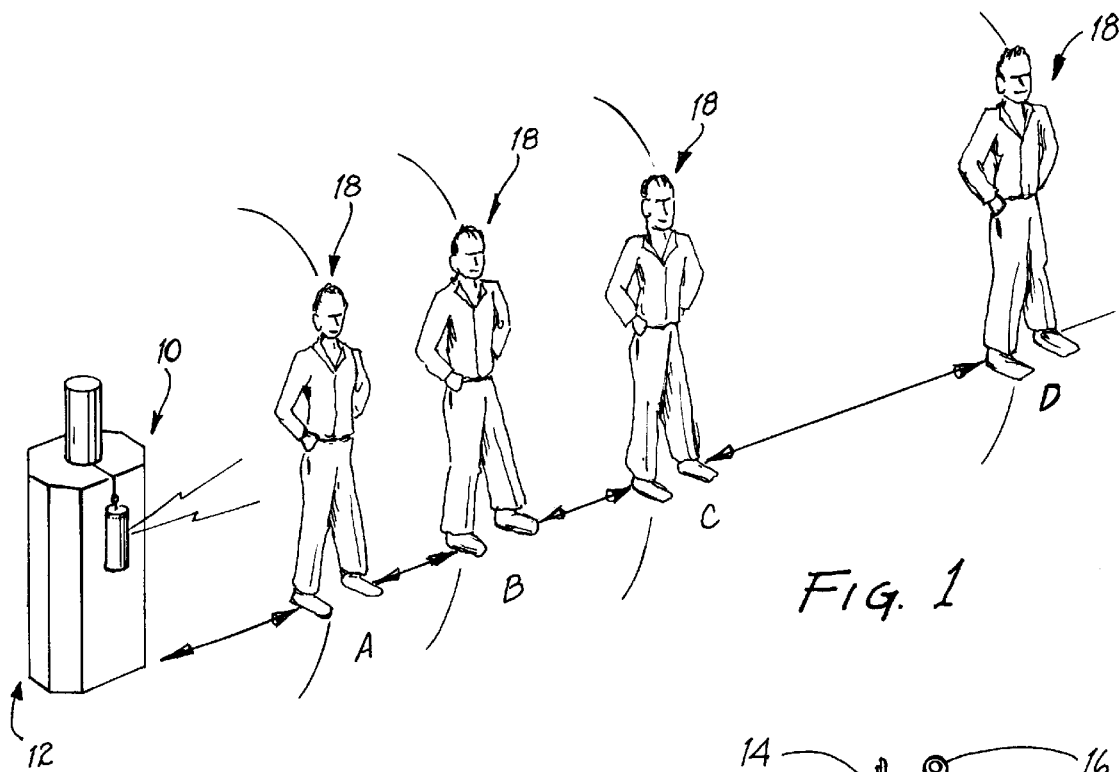
FIG. 1 is a perspective view of the practicing of the method of the present invention, with the positioning of a person at varying distances from an electroacoustic transducer.

Referring now to FIG. 1, a person 18 suffering from a circulatory disorder is positioned near the container 12 with the transducer 10 therein. (While a person 18 is shown as a human, the term "person" as used herein is intended to include animals and humans alike.) The person 18 may be positioned at any distance relative to the transducer 10/container 12 that is determined to be therapeutically beneficial. Tests have indicated that benefit is provided within a range of from approximately one foot to approximately twenty feet—though benefit may be provided outside of this range as well as at any point within this range. Distance A is intended to represent one foot of distance, distance B represents five feet of distance, distance C represents 10 feet of distance, and distance D represents 20 feet of distance.

While FIG. 1 illustrates a person 18 positioned at different points to one side of the transducer 10, it should be noted that the transducer 10 is omni-directional, such that a person 18 could be positioned on any side of the transducer 10—or two or more persons 18 could be positioned on different sides of the transducer 10 simultaneously. Indeed, preferably, persons 18 are placed in chairs surrounding the transducer 10, and receive treatment in this relatively comfortable orientation.

The person 18 should be exposed to acoustic waves from the transducer 10 at any frequency that is determined to be therapeutically beneficial. Tests have indicated that benefit is provided within a range of from one to one thousand Hertz, with particularly good results obtained between four hundred and eight hundred Hertz and optimal results obtained at approximately six hundred Hertz.

The person 18 should be exposed to acoustic waves from the transducer 10 for a period of time that is determined to be therapeutically beneficial. Tests have indicated that benefit is provided by exposure for a period of time ranging from two seconds to one hour, with better results provided by exposure for a period of time ranging from fifteen minutes to forty-five minutes. A range of twenty minutes to thirty minutes is preferred, and an exposure lasting approximately twenty-five minutes appears to provide optimal results. It appears further that, for better results, the treatment should be repeated over time on a weekly or perhaps monthly basis, until the symptoms disappear permanently.

The method of the present invention has been tested on several people suffering from circulatory disorders. Most of those tested experienced a significant alleviation of their symptoms.

It should be noted further that good results have been achieved in certain instances by having a person 18 place the afflicted portion of his or her body in the liquid in the container 12. In one embodiment, the container 12 may be made in a jacuzzi or bath size (or may actually be a jacuzzi), with persons 18 sitting in the container 12 for treatment. When practicing such a method, it is possible for a person 18 to be positioned extremely close to the transducer 10, even less than a distance of one foot.

Although a particular embodiment of the invention has been described in detail for purposes of illustration, various modifications may be made without departing from the spirit and scope of the invention. Accordingly, the invention is not to be limited, except as by the appended claims.

I claim:

1. A method for treating circulatory disorders comprising the steps of:

provi ding a low frequency sonic transducer;

immersing said low frequency sonic transducer in a liquid-containing container;

positioning a person having a circulatory disorder a therapeutically beneficial distance from said container;

wherein said therapeutically beneficial distance is approximately one foot from said container; and exposing said person for a therapeutically beneficial period of time to acoustic waves from said low frequency sonic transducer at a therapeutically beneficial frequency;

wherein said therapeutically beneficial frequency is between approximately four hundred and eight hundred Hertz.

2. The method of claim 1 wherein said therapeutically beneficial distance is approximately five feet from said container.

3. The method of claim 1 wherein said therapeutically beneficial distance is approximately ten feet from said container.

4. The method of claim 1 wherein said therapeutically beneficial distance is approximately twenty feet from said container.

5. The method of claim 1 wherein said therapeutically beneficial period of time is between approximately two seconds and one hour.

6. The method of claim 5 wherein said therapeutically beneficial period of time is between approximately fifteen minutes and forty-five minutes.

7. The method of claim 6 wherein said therapeutically beneficial period of time is between approximately twenty minutes and thirty minutes.

8. The method of claim 7 wherein said therapeutically beneficial period of time is approximately twenty-five minutes.

9. The method of claim 1 wherein said therapeutically beneficial frequency is between approximately one and one thousand Hertz.

10. The method of claim 9 wherein said therapeutically beneficial frequency is approximately 600 Hertz.

11. A method for treating circulatory disorders comprising the steps of:

providing a low frequency sonic transducer;

immersing said low frequency sonic transducer in a liquid-containing container;

positioning a person having a circulatory disorder approximately one foot from said container; and exposing said person for between approximately fifteen minutes and forty-five minutes to acoustic waves from said low frequency sonic transducer at approximately six hundred Hertz.

12. The method of claim 11 wherein said person has atherosclerosis.

13. The method of claim 11 wherein said person has coronary artery disease.

14. The method of claim 11 wherein said person has ischemic heart disease.

15. The method of claim 11 wherein said person has angina pectoris.

16. The method of claim 11 wherein said person has impotence.

* * * * *